United States Patent [19]

Müller et al.

[11] Patent Number: 5,179,186

[45] Date of Patent: Jan. 12, 1993

[54] PHOTOSETTING IMPRESSION MATERIALS

[75] Inventors: Hanns P. Müller, Bergisch Gladbach; Reiner Voigt, Leverkusen; Jens Winkel, Cologne; Peter Schwabe, Leverkusen, all of Fed. Rep. of Germany

[73] Assignee: Bayer Aktiengesellschaft, Leverkusen, Fed. Rep. of Germany

[21] Appl. No.: 706,128

[22] Filed: May 28, 1991

[30] Foreign Application Priority Data

Jun. 7, 1990 [DE] Fed. Rep. of Germany ....... 4018183

[51] Int. Cl.$^5$ .............................................. C08G 18/30
[52] U.S. Cl. ...................................... 528/49; 106/35; 106/38.2
[58] Field of Search ................... 528/49; 106/35, 38.2

[56] References Cited

U.S. PATENT DOCUMENTS 3,891,523  6/1975  Hisamatsu et al. ................... 528/49

FOREIGN PATENT DOCUMENTS 0269071 11/1986 European Pat. Off. .
0204160 12/1986 European Pat. Off. .
0212681  3/1987 European Pat. Off. .
0255286  2/1988 European Pat. Off. .

Primary Examiner—Maurice J. Welsh
Attorney, Agent, or Firm—Sprung Horn Kramer & Woods

[57] ABSTRACT

A method of making a dental impression which comprises applying to the structure of which an impression is to be made a special prepolymer. The prepolymer is composed of units of at least one macrodiol, at least one aliphatic polyisocyanate, and an unsaturated monoalcohol as chain terminator, wherein the average functionality of the prepolymer based on the unsaturated groups is >2.

7 Claims, No Drawings

PHOTOSETTING IMPRESSION MATERIALS

The invention relates to photosettable impression materials, preferably for dental applications. The impression compositions described within the scope of the present invention are used for preparing impressions of items of which a three-dimensional copy is to be prepared. The impression compositions can be employed preferably in dentistry in the preparation of inlays, crowns, bridges and dentures. It is possible with their aid to prepare a negative of the jaw situation, into which subsequently modelling plaster, for example, is poured. The model obtained in this way is used as basis for further work by the dental technician. In order to guarantee an adequate accuracy to fit of the item produced by the technician, the impression compositions which are used must display a minimum alteration in dimensions.

A number of materials are used for this application: for example polysulphides, polyethers, condensation- and addition-crosslinking siloxanes. All these materials are two-component systems in which, in accordance with the manufacturer's instructions, a basic paste must be mixed homogeneously with a catalyst paste, in a particular ratio by weight or volume, within 30 to 40 seconds and the mixture must subsequently, in a maximum of 90 seconds, be placed on the areas of which an impression is required. Faults in manipulation, such as inaccurate dosage and insufficient mixing of the components, as well as incorporation of air bubbles, may result in useless impressions. The materials described in the present invention take the form of pasty single-component materials which can be placed directly from an opaque tube or cartridge on the impression tray or sprayed onto the area of which an impression is required, and are subsequently crosslinked by exposure to light—preferably with a wavelength between 300 and 600 nm—to give a rubber-elastic impression.

Photosetting impression materials have already been disclosed. Compared with the silicone acrylates described in U.S. Pat. No. 4,575,545, the materials according to the invention display distinctly reduced inhibition layers. Compared with the urethane diacrylates described in European Patent Applications 257,777, 255,286, 269,071 and 173,088, the more highly functionalized acrylates according to the invention surprisingly show a smaller alteration in dimensions. This is a considerable advantage for the use as dental impression material.

One problem when making impressions of teeth is often caused by thin films of the impression material being torn off and remaining in the gingival pockets. These residues may bring about serious inflammation. This problem can likewise be solved because of the high tensile strengths of the impression materials according to the invention.

It has now been found that photosetting prepolymers as impression materials composed of, in each case, at least one macrodiol, preferably selected from polyetherdiols of a molecular weight range of 400 to 20,000,, one aliphatic polyisocyanate, where appropriate low molecular weight diols or diamine chain extenders, unsaturated monoalcohols, containing end groups, as chain terminators and customary auxiliaries and additives, characterized in that the average functionality of the prepolymers based on the unsaturated groups is $>2$, do not have the disadvantage of the products of the state of the art.

Preferably used for this purpose as impression materials are those photosetting prepolymers in which hydroxyacrylates or -methacrylates are employed as chain terminators, e.g. glycerol-diacrylate, glycerol-dimethacrylate, glycerol-acrylate-methacrylate, pentaerythritol-triacrylate, pentaerythritol-trimethacrylate, or mixed esters of pentaerythritol with acrylic acid and methacrylic acid where appropriate mixed with hydroxyethylacrylate or methacrylate, with the proviso that the average functionality of the prepolymers is $>2$.

Particularly preferred are those in which aliphatic and/or cycloaliphatic diisocyanates, where appropriate mixed with tri- and tetraisocyanates, are employed for building up the unsaturated prepolymers containing end groups, with the proviso that the average functionality of the prepolymers based on the unsaturaged groups is $>2$.

A process for preparing photosetting impression materials has also been found and is characterized in that 1.7 to 3, preferably 1.8 to 2.2, moles of diisocyanate (mixture) are used per 1 mole of macrodiol of molecular weight range 22 400 where appropriate mixed with low molecular weight diols of molecular weight range 62–400, and the resulting intermediate is reacted with hydroxyethyl acrylate or methacrylate and poly(meth-)acrylic esters containing OH groups to give prepolymers whose average functionality based on the unsaturated groups is $>2$.

The urethane acrylates which can be used according to the invention contain at least three acrylic or methacrylic esters. They can be prepared by reacting aliphatic and/or cycloaliphatic diisocyanates with macrodiols, for example dihydroxy polyethers of the average molecular weight range Mn from 400 to 6000, optionally also adding aliphatic and/or cycloaliphatic dihydric alcohols of an average molecular weight Mn from 62 to $<400$ in addition, and reacting the resulting prepolymers with hydroxyalkyl acrylates or methacrylates, it also being possible optionally to use in addition aliphatic and/or cycloaliphatic diamines with primary amino groups with a molecular weight of Mn from 60 to 300, by a) adding hydroxyalkyl polyacrylates or hydroxyalkyl polymethacrylates or mixed hydroxyalkyl acrylates/-methacrylates alone or mixed with hydroxyethyl acrylate or methacrylate, also employing b) 1.7 to 3, preferably 1.8 to 2.2 moles of diisocyanate (mixture) per 1 mole of macrodiol where appropriate mixed with macromolecular diols and/or diamines.

The components are reacted at temperatures from 20 to 150° C., preferably from 60° to 120° C.

The diamines which are optionally employed are used to adjust the particular molecular weight which is required.

Suitable diisocyanates are, in particular, those with aliphatically and/or cycloaliphatically bonded isocyanate groups of the formula $Q(NCO)_2$, in which Q represents an aliphatic hydrocarbon radical with 2 to 12 carbon atoms or a cycloaliphatic or mixed aliphatic-cycloaliphatic hydrocarbon radical with 4 to 15 carbon atoms.

Examples of diisocyanates of this type are ethylene diisocyanate, tetramethylene diisocyanate, hexamethylene diisocyanate, dodecamethylene diisocyanate, cyclobutane 1,3-diisocyanate, cyclohexane 1,3- and 1,4- diisocyanate or 1-isocyanato-3,3,5-trimethyl-5- isocyanatomethylcyclohexane, 4,4'-diisocyanato-dicyclohexylmethane and any desired mixtures of diisocyanates of this type. Cycloaliphatic or mixed aliphatic-cycloaliphatic diisocyanates are preferably empliyed in the process according to the invention. 1-Isocyanato-3,3,5-trimethyl-5-isocyanato-methyl-cyclohexane (isophorone diisocyanate) is particularly preferred.

Suitable dihydroxy polyethers are likewise those of the type known per se and are prepared, for example, by self-polymerization of epoxides such as ethylene oxide, propylene oxide, butylene oxide, tetrahydrofuran, styrene oxide or epichlorohydrin, for example in the presence of $BF_3$, or by addition of these epoxides, where appropriate in a mixture or successively, onto starting components with reactive hydrogen atoms such as alcohols or amines, for example water, ethylene glycol, 1,3- or 1,2-propylene glycol, 4,4'-dihydroxydiphenylpropane, aniline. Preferred polyethers are those which predominantly (up to 90% by weight based on all Oh groups present in the polyether) have primary OH groups.

Suitable diamines are preferably aliphatic, cycloaliphatic or mixed aliphatic-cycloaliphatic diamines of the molecular weight range 60 to 300 which have primary amino groups. Examples are ethylenediamine, tetramethylenediamine, hexamethylenediamine, 4,4'-diamino-dicyclohexylmethane, 1,4-diaminocyclohexane, 4,4'-diamino-3,3'-dimethyl-dicyclohexylmethane or 1-amino-3,3,5-trimethyl-5-aminomethyl-cyclohexane (isophoronediamine). 4,4'-Diaminodicyclohexylmethane or the last-mentioned isophoronediamine are very particularly preferably employed.

Examples of suitable dihydric alcohols are ethylene glycol, 1,2- and 1,3-propylene glycol, 1,4- and 2,3-butylene glycol, 1,6-hexanediol, 1,8-octanediol, neopentyleneglycol, cyclohexanedimethanol, 1,4-bis-hydroxymethylcyclohexane, 2-methyl-1,3-propanediol, 3-methyl-1,5-pentanediol, furthermore diethylene glycols, dipropylene glycol, polypropylene glycols, dibutylene glycols and polybutylene glycols.

Suitable hydroxyacrylates and -methacrylates are glycerol diacrylate, glycerol dimethacrylate, glycerol acrylate meth-acrylate, pentaerytritol triacylate, pentaerythritol trimethacrylate and mixed esters of pentaerythritol with acrylic acid and methacrylic acid. Also suitable according to the invention are mixtures of the described poly(meth)acrylic esters which contain OH groups with hydroxyethyl acrylate or methacrylate.

Mixtures of the described urethane acrylates with, in principle, all radically settable monomers are also suitable according to the invention.

Particularly suitable for this purpose are the methacrylates which are known per se, in monofunctional or polyfunctional form and which can be employed alone or in mixtures. Examples are methyl methacrylate, isobutyl methacrylate, cyclohexyl methacrylate, ethylene glycol dimethacrylate, diethylene glycol dimethacrylate, polyethylene glycol dimethacrylate, butanediol dimethacrylate, hexanediol dimethacrylate, decanediol dimethacrylate, dodecanediol dimethacrylate, bisphenol A di-methacrylate, trimethylolpropane trimethacrylate, and also bis-GMA and the reaction products of isocyanates, especially di- and/or triisocyanates and methacrylagtes containing OH groups.

Examples of the latter are the reaction products of 1 mole of hexamethylene-diisocyanate with 2 moles of (2-hydroxyethyl)-methacrylate, of 1 mole of tris-(6-isocyanatohexyl)-isocyanurat with 3 moles of trimethyl-hexamethylene-diisocyanate with 2 moles of hydroxyethyl-methacrylate.

The proportion of these compounds in the mixture with the urethane acrylate(s) varies between 10 and 70 per cent by weight, preferably between 20 and 50 per cent by weight.

The compounds can be cured with catalysts which are known per se and which can be activated by radiation. The use of a photosensitizer together with a reducing agent is preferred. Examples of photosensitizers are α-diketones such as 9,10-phenanthrenequinone, diacetyl, furil, anisil, 4,4', dichlorobenzil and 4,4'-dialkoxybenzil. Camphorquinone is preferably used. Examples of reducing agents are amines such as cyanoethylmethylaniline, dimethylaminoethyl metacrylate, n-butylamine, triethylamine, triethanolamine, N,N-diemthylaniline or N-methyldiphenylamine.

They can also be cured with catalysts known per se for hot or redox polymerization. Thus for the hot polymerization with peroxides such as dibenzoyl peroxide, dilauroyl peroxide, tert.-butyl peroctoate or tert.-butyl perbenzoate, and also with α, α-azo-bis-(isobutyroethyl ester)-benzopinacol and 2,2'-dimethylbenzopinacol.

Suitable for the so-called redox polymerization is a system composed of a peroxide compound and a reducing agent, for example based on tertiary aromatic amines. Examples of peroxides are: dibenzoyl peroxide, dilauroyl peroxide and di-4-chlorobenzoyl peroxide.

Examples of tertiary aromatic amines which may be mentioned are N,N-dimethyl-p-toluidine, bis-(2-hydroxyethyl)-p-toluidine, bis-(2-hydroxyethyl)-3,5-dimethylaniline and N-methyl-N-(2-methylcarbamoyloxypropyl)-3,5-dimethylaniline.

The peroxide- and amine-containing monomer mixtures are stored separately until used.

The said catalysts are used in amounts of 0.01 to 10% by weight based on the polymerizable material, in particular in amounts of 0.1 to 5% by weight.

Depending on the purpose for which the material is used, the materials can also contain inorganic or organic fillers. Examples of suitable inorganic fillers are: rock crystal, cristobalite, quartz glass, highly disperse silica, aluminum oxide and glass ceramics, for example lanthanum and zirconium containing glass ceramics (German Patent Specification 2,347,591). The inorganic fillers are preferably pretreated with an adhesion promoter to improve the bonding to the polymer matrix. The adhesion promotion can be achieved, for example, by treatment with organolsilicon compounds (Progress in Organic Coatings 11, 297–308 (1983)). Preferably employed is 3-methacryloyloxypropyl-trimethoxysilane. It may also be advantageous to employ side-by-side several fillers which have a differing particle diameter and/or a different silane content.

Examples of suitable organic fillers are plastic dusts and beads based on polyethylene, polypropylene, polyvinyl chloride, polyvinyl acetate, polystyrene, polyamide, polycarbonate, polyester, polyacrylate and polymethacrylate.

The proportion of filler in the mixture is generally 0 to 80% by weight, preferably 10 to 70% by weight. It is also possible to add organic polymers or copolymers to the material. The customary auxiliaries such as stabilizers, light stabilizers, plasticizers, fragrances and colorings can also be present. The following composition may be mentioned by way of example:

100 parts by weight of paste contain:
a) 50–95 parts by weight of urethane acrylate b) 0–50 parts by weight of comonomer
c) 0–80 parts by weight of filler
d) 0–5 parts by weight of initiator for the radical polymerization
e) 0–5 parts by weight of auxiliaries.

The impression compositions according to the invention are used to fill opaque tubes or cartridges. In use, a composition of low or moderate viscosity can be applied by means of a spray device to the row of teeth of which an impression is required. Then a highly viscous composition in an impression tray composed of a transparent material such as polymethacrylate, polycarbonate or polystyrene is pressed onto the row of teeth around which the composition of low or moderate viscosity has been sprayed. Subsequently the compositions which have flowed into one another are polymerized by exposure to visible light with a wavelength between 300 and 600 nanometers by means of a light guide. A negative with accurate detail of the row of teeth of which an impression has been produced is obtained, into which subsequently modelling plaster, for example, can be poured.

Besides the use as impression compositions, the compositions can be employed both in the photosetting and in the radical crosslinking variant as relining material, which remains soft, for dentures. Because the denture material generally consists of polymethacrylate, there is bonding of the denture and relining material because of the same chemical basis when the compositions according to the invention are used as relining material.

EXAMPLES OF PHOTOSETTING IMPRESSION COMPOSITIONS

EXAMPLES 1

(Preparation of a urethane methacrylate)

4,000 g (1 mole) of a polyether which was started on propylene glycol and underwent polyaddition initially with 87 parts by weight of propylene oxide and then with 13 parts by weight of ethylene oxide (OH number=28, MW=4,000, $\eta$ 25° C.=800 mPa.s) are dried at 120° C. under waterpump vacuum for 1 h and then 400 g (1.8 mole) of isophorone diisocyanate and 0.1 g of tin octoate are added to the mixture. The mixture is stirred at 120° C. under nitrogen for 1 h and then the NCO content of the prepolymer (I) is determined (NCO found 1.33%; NCO calculated 1.53%).

0.1 g of 2,6-di-tert.-butyl-4-methyl-phenol, 49.8 g of glycerol dimethacrylate and 0.35 g of tin(II) octoate are added to 600 g of the NCO prepolymer (I) obtained in this way. The mixture is heated to 60° C. and it is all stirred for 48 h. After this free NCO is no longer detectable. A tetrafunctional urethane methacrylate with a viscosity of 66 Pa.s at 20° C. obtained.

EXAMPLE 2

(Preparation of a urethane acrylate methacrylate)

The process is carried out as described in Example 1 but with the difference that 0.1 g of 2,6-di-tert.-butyl-4-methyl-phenol and 46.7 g of glycerol monoacrylate monomethacrylate and 0.3 g of tin octoate are added to 600 g of the NCO prepolymer (I). The mixture is stirred at 60° C. for 48 h. After this free NCO is no longer detectable. A tetrafunctional urethane acrylate methacrylate with a viscosity of 237 Pa.s at 20° C. is obtained in this way.

EXAMPLE 3

(Preparation of a urethane methacrylate)

The process is carried out as described in Example 1 but with the difference that 0.1 g of 2,6-di-tert.-butyl-4-methylphenol, 24.9 g of glycerol dimethacrylate, 14.2 g of hydroxyethyl methacrylate and 0.2 g of tin(II) octoate are added to 600 g of the NCO prepolymer (I). The mixture is stirred at 60° C. for 48 h. After this free NCO is no longer detectable. A trifunctional urethane methacrylate with a viscosity of 42 Pa.s at 20° C. is obtained in this way.

EXAMPLE 4

(Preparation of a urethane methacrylate) Comparison

The process is carried out as described in Example 1, but with the difference that 0.1 g of 2,6-di-tert.-butyl-4-methylphenol, 28.4 g of hydroxyethyl methacrylate and 0.2 g of tin(II) octoate are added to 600 g of the NCO prepolymer (I). The mixture is stirred at 60° C. for 48 h. After this free NCO is no longer detectable. A difunctional urethane methacrylate with a viscosity of 58 Pa.s at 20° C. is obtained in this way.

EXAMPLE 5

(Activation of the urethane (meth)acrylates)

99.45% urethane (meth)acrylate from Examples 1, 2, 3 or 4
0.25% diallylsulphonamide
0.10% ionol
0.20% camphorquinone are mixed in a Rotavapor in the dark for 15 hours.

EXAMPLE 6

(Preparation of an impression composition)

85.71% urethane (meth)acrylate from Example 1, 2, 3 or 4, activated as in Example 5
14.27% Syloid ED 5 (supplied by Grace)
0.02% Sicomet colour red B 12085 (BASF)

The raw materials were mixed homogeneously in a planetary mixer in the dark. The impression composition of moderate viscosity was used to fill opaque cartridges.

EXAMPLE 7

(Preparation of an impression composition)

60.00% of urethane (meth)acrylate from Example 1, 2, 3 or 4, activated as in Example 5
10.00% of Syloid ED 5 (supplied by Grace)
29.95% of extremely finely ground cristobalite
0.05% of Sicomet colour blue P 74160 (BASF)

The starting materials were mixed homogeneously in the dark in a planetary mixer. The highly viscous impression composition was used to fill tubes.

EXAMPLE 8

(Tests on the impression compositions after photosetting)

Both the activated urethane (meth)acrylates from Example 5 and the impression compositions, formulated therefrom, from Examples 6 and 7 were placed in moulds for test specimens and irradiated in a Dentacolor light oven for 30 seconds. After this the Shore A hardness, the alteration in dimensions according to specification No. 19 of the American Dental Association and the tensile strength according to DIN 53 504 were measured. The results are compiled in Table 1.

TABLE 1

Results of tests on impression material after photosetting

| Composition (Example) | Urethane (meth)acrylate (Example) | Hardness (Shore A) [%] | Alteration in dimensions [%] | Tensile strength [N/mm$^2$] |
|---|---|---|---|---|
| Unfilled (5) | Tetrafunctional UMA (1) | 48 | 0.19 | 1.9 |
| | Tetrafunctional UAMA (2) | 47 | 0.17 | 1.7 |
| | Trifunctional UMA (3) | 47 | 0.22 | 1.9 |
| | Difunctional UMA (4) | 45 | 0.38 | 0.9 |
| Filled moderate viscosity (6) | Tetrafunctional UMA (1) | 70 | 0.11 | 6.9 |
| | Tetrafunctional UAMA (2) | 68 | 0.10 | 6.5 |
| | Trifunctional UMA (3) | 70 | 0.12 | 6.7 |
| | Difunctional UMA (4) | 66 | 0.31 | 4.2 |
| Filled high viscosity (7) | Tetrafunctional UMA (1) | 82 | 0.06 | 10.9 |
| | Tetrafunctional UAMA (2) | 80 | 0.06 | 10.9 |
| | Trifunctional UMA (3) | 81 | 0.07 | 10.5 |
| | Difunctional UMA (4) | 78 | 0.22 | 7.2 |

It will be appreciated that the instant specification is set forth by way of illustration and not limited, and that various modifications and changes may be made without departing from the spirit and scope of the present invention.

What is claimed is:

1. A method of making a dental impression which comprises applying the structure of which an impression is to be made a photosettable prepolymer composed of units of at least one macrodiol, at least one aliphatic polyisocyanate, and an unsaturated monoalcohol as chain terminator, wherein the average functionality of the prepolymer based on the unsaturated group is >2, and exposing the prepolymer to light thereto to effect its polymerization.

2. A method according to claim 1, wherein the macrodiols are selected from polyetherdiols of a molecular weight range from 400 to 200,000.

3. A method according to claim 1, the prepolymer further including units of a low molecular weight diol or diamine.

4. A method according to claim 1, wherein the chain terminator comprises at least one member selected from the groups consisting of a hydroxyacrylate or -methacrylate, glycerol-diacrylate, glyerol-dimethacrylate, glycerol-acrylate-methacrylate, pentaerythritol-triacrylate, pentaerythritol-trimethacrylate, and mixed esters or pentaerythritol with acrylic acid and methacrylic acid.

5. A method according to claim 1, the prepolymer further including units of hydroxyethyl acrylate or methacrylate.

6. A method according to claim 1, wherein the polyisocyanate of the prepolymer includes units of at least one of tri- and tetraisocyanates.

7. A method according to claim 1, wherein the prepolymer is prepared by reacting 1.7 to 3 moles of diisocyanate per mole of macrodiol of molecular weight <400 and reacting the resulting intermediate with a poly(meth)acrylic ester containing OH groups.

* * * * *

UNITED STATES PATENT AND TRADEMARK OFFICE
CERTIFICATE OF CORRECTION

PATENT NO. : 5,179,186
DATED     : January 12, 1993
INVENTOR(S) : Muller et al.

It is certified that error appears in the above-identified patent and that said Letters Patent is hereby corrected as shown below:

Col. 7, line 30   After " applying " insert -- to --

Col. 8, line 23   Delete " groups " and substitute -- group --

Signed and Sealed this

Twenty-eighth Day of June, 1994

Attest:

BRUCE LEHMAN

Attesting Officer    Commissioner of Patents and Trademarks